United States Patent
Vatti et al.

(10) Patent No.: US 11,931,575 B2
(45) Date of Patent: Mar. 19, 2024

(54) COCHLEAR IMPLANT SYSTEM WITH OPTIMIZED FRAME CODING

(71) Applicant: Oticon Medical A/S, Smørum (DK)

(72) Inventors: Marianna Vatti, Smørum (DK); Kai Dang, Xiangyang (CN); Pierre Stahl, Vallauris (FR); Manuel Segovia Martinez, Vallauris (FR); Dan Gnansia, Vallauris (FR); Bradford Backus, Vallauris (FR)

(73) Assignee: Oticon Medical A/S, Smørum (DK)

( * ) Notice: Subject to any disclaimer, the term of this patent is extended or adjusted under 35 U.S.C. 154(b) by 246 days.

(21) Appl. No.: 17/407,940

(22) Filed: Aug. 20, 2021

(65) Prior Publication Data

US 2022/0054836 A1    Feb. 24, 2022

(30) Foreign Application Priority Data

Aug. 21, 2020  (EP) .................................. 20192175

(51) Int. Cl.
| | |
|---|---|
| *A61N 1/36* | (2006.01) |
| *A61N 1/02* | (2006.01) |
| *A61N 1/05* | (2006.01) |
| *A61N 1/08* | (2006.01) |
| *G16H 20/40* | (2018.01) |

(52) U.S. Cl.
CPC ......... *A61N 1/36038* (2017.08); *A61N 1/025* (2013.01); *A61N 1/0541* (2013.01); *A61N 1/08* (2013.01); *G16H 20/40* (2018.01)

(58) Field of Classification Search
CPC .. A61N 1/36038; A61N 1/025; A61N 1/0541; A61N 1/08; G16H 20/40
See application file for complete search history.

(56) References Cited

U.S. PATENT DOCUMENTS

| | | | |
|---|---|---|---|
| 4,207,441 A | 6/1980 | Ricard et al. | |
| 4,532,930 A | 8/1985 | Crosby et al. | |
| 9,084,893 B2 * | 7/2015 | Vandali | .................... G10L 25/90 |
| 9,713,715 B2 * | 7/2017 | Smith | .................. H04R 25/505 |

FOREIGN PATENT DOCUMENTS

| | | | |
|---|---|---|---|
| EP | 0 247 649 A1 | 12/1987 | |
| EP | 2959939 A2 * | 12/2015 | ........... A61N 1/0529 |
| WO | WO 91/03913 A1 | 3/1991 | |
| WO | WO 2013/186743 A2 | 12/2013 | |

* cited by examiner

*Primary Examiner* — Allen Porter
*Assistant Examiner* — Daniel Tehrani
(74) *Attorney, Agent, or Firm* — Birch, Stewart, Kolasch & Birch, LLP

(57) ABSTRACT

The disclosure relates to a cochlear implant system, and more particularly, the disclosure relates to a processor unit which includes a switching mean configured to switch between using a fixed stimulation frame onset or a variable stimulation frame onset for frame coding a plurality of stimulation pulses into a one or more stimulation frames.

17 Claims, 9 Drawing Sheets

COCHLEAR IMPLANT SYSTEM WITH OPTIMIZED FRAME CODING

FIELD

The present disclosure relates to a cochlear implant system. More particularly, the disclosure relates to a processor unit which includes a switching mean configured to switch between using a fixed stimulation frame onset or a variable stimulation frame onset for frame coding a plurality of stimulation pulses into a one or more stimulation frames.

BACKGROUND

Known multichannel cochlear implants (CI) encode environmental sounds directly into a plurality of stimulation pulses which is then frame coded into one or more stimulation frames using specific waveform strategies, such as the Continuous Interleaved Sampling (CIS). The frame coded plurality of stimulation pulses is then transmitted to the inner ear via electrical stimulations. The electrical stimulation is provided by an electrode array which comprises a plurality of electrodes. The Continuous Interleaved Sampling (CIS) strategy aims to sequentially stimulate the cochlea by decomposing the environmental sounds into spectral bands accorded to the placement of each plurality of electrodes of the electrode array. Each electrode is generating fixed-rate charge-modulated currents according to its respective bandpass filtered envelope. This modulation over time is supposed to recreate the neural stimulation pattern (temporal coding).

It may be that the temporal coding is not ideally conveyed in an CIS-like implementation. A perceptual example illustrating this litigation is pitch, which was known to be place coding related even if a high amount of evidence showed that temporal coding is playing an important role in pitch perception. For example, in temporal coding it was shown that pitch discrimination was more strongly conveyed using variable stimulation frame onset rather than fixed stimulation frame onset during frame coding. The frame coding aims to generate a one or more stimulation frames which transmits the most possible and coherent preselected features or audio components characterizing the environmental sound as electrical stimulation pulses with either a fixed stimulation frame onset or a variable stimulation frame onset.

The CIS waveform strategy is based on frame coded stimulation pulses delivered to corresponding electrodes in a time-interleaved fashion. The pulses will sequentially stimulate from the most basal to the most apical electrode (frame). Therefore, this strategy requires a fix period of time for re-stimulating the same electrode. The CIS waveform strategy relies on a fixed stimulation frame onset.

In known cochlea implant systems information and energy are transmitted transcutaneously between an external unit and an implantable unit on the same modulated radio frequency (RF) carrier. The energy provided to the implantable unit may be proportional to the power level and the active time of the RF transmission. In order to provide a stable control, the external unit provides a constant active time of the RF transmission per frame. The RF frame is built by a series of pulses that either transmits the information or control the stimulation or pulses that transmits the energy.

An optimal frame onset strategy does not provide a stable energy control only with a constant RF length (due to the variable nature of the frame length).

Therefore, there is a need to provide a solution that addresses at least some of the above-mentioned problems.

SUMMARY

An aspect of the disclosure is to provide an improved frame coding for obtaining an improved temporal information provided via electrical stimulation of the auditory nerve fibers.

A further aspect of the disclosure is to provide a stable energy control of the implantable unit.

The aspect of the disclosure is achieved by a cochlear implant system which may comprise a receiving unit configured to receive an acoustical signal and transmit an audio signal based on the acoustical signal. The receiving unit may be arranged in an external unit and/or an implantable unit. The external unit may be arranged on a skin of a user, e.g. on a head or an ear of the user, and the implantable unit may be arranged below the skin of the user, e.g. between the skin and a skull of the head. The receiving unit may comprise one or more microphones and/or a radio frequency interface configured to communicate wirelessly with an auxiliary device. The wireless communication may be based on Bluetooth, Bluetooth low energy or any short/long range communication protocol.

The cochlear implant system may further comprise a processor unit configured to receive and divide the audio signal into a plurality of band limited audio signals and to generate a plurality of stimulation pulses based on sampling of the plurality of band limited audio signals, and wherein each of the plurality of band limited audio signals is sampled with a temporal onset. One or more audio components are determined for each of the sampled plurality of stimulation pulses.

The processor unit may be configured to generate a sequence of events of each of the plurality of band limited audio signals, and where each event of the sequence of events is detected when a phase of the band limited audio signal exceeds a phase threshold, and wherein the phase threshold may be any value between 0 and $2\pi$. The temporal onset may be equal to an event rate of the sequence of events. At each event a stimulation pulse is generated based on one or more audio components extracted from the audio signal and/or from each of the sampled plurality of band limited audio signals, where the sampling is based on a waveform strategy, a feature extraction strategy, or a hybrid between the waveform strategy and the feature extraction strategy.

The processor unit may include a filter bank which comprises numbers of bandpass filters each configured for generating a band limited audio signal which includes a frequency band of the audio signal, and where the frequency band includes a range of frequencies of the audio signal. The filter bank may consist of 20 or more bandpass filters covering the frequencies from 80 Hz to 10.000 HZ. Each filter may be allocated to an electrode of the electrode array, and each electrode may be assigned to a specific frequency range.

The sampling of the plurality of band limited audio signals may be based on a waveform strategy, such as Continuous Interleaved Sampling (CIS) or Spectral Peak (SPEAK), or based on a feature extraction strategy including determination of Temporal Fine Structure (TFS) of the audio signal, or based on a hybrid strategy between CIS and the feature extraction strategy.

The feature extraction strategy may be configured to extract features of the full bandwidth of the audio signal which allows identification of features without constraining analysis to individual channel bands. In this example, the processor unit may be configured to receive the audio signal and generate one or more band limited audio signals of the audio signal based on sampling of the one or more band limited audio signals, wherein the one frequency band includes the full bandwidth of the audio signal.

Thereby, the extracted features are more accurately determined in comparison to when the audio signal is first divided into multiple band limited audio signals by a filter bank, and thereafter performing the feature extraction on each of the interested band limited audio signals.

The one or more audio components may include the extracted feature(s) which characterizes ideally the acoustical signal received by the receiving unit. The extracted features may be a fundamental frequency, harmonic frequencies relative to the fundamental frequency of the audio signal, energy at and around the fundamental frequency and harmonics of the audio signal, and/or phase at and around the fundamental frequency and harmonics of the audio signal.

The waveform strategy may extract an amplitude, a phase, a fundamental frequency or harmonic frequencies of a band limited audio signal of the plurality of band limited audio signals. In this example, the processor unit may be configured to receive the audio signal and to generate one or more band limited audio signals of the audio signal or a plurality of band limited audio signals. Each of the one or more band limited audio signals or of the plurality of band limited audio signals may include an oscillating envelope. The amplitude, phase, fundamental frequency or harmonic frequencies may be derived from the oscillating envelope by rectification and lowpass filtering. The extracted amplitude, phase, fundamental frequency and/or harmonic frequencies may be part of the one or more audio components characterizing ideally the acoustical signal received by the microphone unit.

The one or more audio components may comprise a plurality of amplitudes, phase, fundamental frequencies and/or harmonic frequencies which characterize ideally the oscillating envelope of the acoustical signal, and/or the one or more audio components may comprise the extracted features which characterizes the acoustical signal.

The audio components may include a fundamental frequency, harmonic frequencies relative to the fundamental frequency of the audio signal, energy at and around the fundamental frequency and harmonics of the audio signal, and/or phase at and around the fundamental frequency and harmonics of the audio signal.

The processor unit may be configured to generate a sequence of events for each of the plurality of band limited audio signals, and where each event of the sequence of events is determined when a phase of the bandpass audio signal exceeds a phase threshold. The phase threshold may be any value between 0 and $2\pi$. The temporal onset may be equal to an event rate of the sequence of events.

The cochlear implant system may further comprise an electrode array including a plurality of electrodes. The electrode array may be wired connected to the implantable unit and implanted into a cochlea of the use of the system, and wherein the electrode array is configured to transfer stimulation pulses, as electrical stimulations, to the auditory nerve fibers of the cochlea.

The acoustical signal may be an acoustic wave which includes acoustic information which is around the user.

For obtaining an optimal temporal information provided by stimulation pulses in dependence of the acoustic signal, the processor unit may include a switching mean configured to switch between using a fixed stimulation frame onset or a variable stimulation frame onset for frame coding the plurality of stimulation pulses into one or more stimulation frames. The switching mean is configured to switch between the fixed stimulation frame onset and the variable stimulation frame onset based on the one or more audio components, and wherein the electrode array is configured to stimulate auditory nerves of a user of the cochlear implant system based on the frame coded plurality of stimulation pulses.

The purpose of frame coding is to time the transferring of the frame coded plurality of stimulation pulses to the implantable unit such that the auditory nerve fibers of the user receives as much temporal information as possible provided by the stimulation pulses. The frame coding produces an electrodogram which includes the information about which electrodes of the electrode array are to be activated and when to be activated for stimulating the auditory nerve fibers with the stimulation pulse.

The temporal information may include one or more audio components, such as features extracted from the acoustical signal or extracted envelope information characterizing the acoustical signal.

Within a stimulation frame of the one or more stimulation frames an electrode of the electrode array may only be activated once, which means, the stimulation frame may only include one stimulation pulse for each electrode For communicating a plurality of stimulation pulses to the implantable unit of the cochlear implant system and then to the electrode array, the plurality of stimulation pulses needs to be organized into the one or more stimulation frames provided by the frame coding, and the plurality of stimulation pulses may then be transferred to the implantable unit sequentially and in a determined order within the stimulation frame. For example, the plurality of stimulation pulses may be organized in an order which is ascending or descending in relation to the frequency content of each of the plurality of stimulation pulses. For example, the electrode which is either the most basal electrode or the most apical electrode of the electrodes to be activated within the stimulation frame will be activated first.

The switching mean may be configured to switch between the fixed stimulation frame rate or the variable stimulation frame rate based on the one or more audio components which may include envelope information and/or features extracted from the audio signal. For example, the switching mean may be configured to switch to the fixed stimulation frame onset when a fundamental frequency of a stimulation pulse is above a frequency threshold and that an energy of the fundamental frequency is above an energy threshold, and the switching mean may be configured to switch to the variable stimulation frame onset when the fundamental frequency is below the frequency threshold and the energy of the fundamental frequency is above the energy threshold.

The switching mean may be configured to switch between the fixed stimulation frame rate or the variable stimulation frame rate based on the one or more audio components which may include envelope information and/or features extracted from the audio signal. For example, the switching mean may be configured to switch to the fixed stimulation frame onset when a fundamental frequency of a stimulation pulse is above a frequency threshold, and the switching mean may be configured to switch to the variable stimulation frame onset when the fundamental frequency is below the frequency.

The switching mean may be configured to switch to the fixed stimulation frame onset when the energy in dB is above an energy threshold, and the switching mean may be configured to switch to the variable stimulation frame onset when the energy in dB is below the energy threshold.

If at least one stimulation pulse of the plurality of stimulation pulses has an energy at the fundamental frequency which is above the energy threshold, and the fundamental frequency is below the frequency threshold, the plurality of stimulation pulses are all frame coded using variable stimulation rate.

If at least one stimulation pulse of a group of stimulation pulses of the plurality of stimulation pulses has an energy at the fundamental frequency which is above the energy threshold, and the fundamental frequency is below the frequency threshold, the group of stimulation pulses are all frame coded using variable stimulation rate.

The frequency threshold may be between 100 Hz and 4000 Hz, 300 Hz and 3500 Hz, or 30 Hz and 3000 Hz.

The energy threshold may be between 40 dB and −20 dB, −20 dB and −30 dB, or −25 dB and −30 dB.

The switching mean may be configured to switch to the fixed stimulation frame onset when the audio components relate to an unvoiced speech, or switch to the variable stimulation frame onset when the audio components relate to a voiced speech. The processor unit is configured to determine whether the acoustical signal includes voice or unvoiced speech based on analysis of the one or more audio components extracted from the sampling of the plurality of band limited audio signals and the frequency spectrum. For example, if the audio signal includes voice speech, the plurality of stimulation pulses of the one or more stimulation frames includes fundamental frequencies which are below the frequency threshold, the switching mean is then configured to switch to variable stimulation frame onset, however, if the audio signal relates to an unvoiced speech, the plurality of stimulation pulses of the one or more stimulation frames includes fundamental frequencies which are above the frequency threshold, the switching mean is then configured to switch to fixed stimulation frame onset. Thereby, the system can optimize the amount of temporal information provided to the auditory nerves fibers according to the content of the audio signal.

The processor unit may be configured to provide a first frame coding scheme and a second frame coding scheme for frame coding the plurality of stimulation pulses into the one or more stimulation frames for the fixed stimulation frame onset and the variable stimulation frame onset, respectively. By having different frame coding schemes for the fixed stimulation frame onset and the variable stimulation frame onset improves even more the temporal information provided to the auditory nerves fibers.

The first frame coding scheme may provide frame coding of a group of stimulation pulse of the plurality of stimulation pulses to a stimulation frame of the one or more stimulation frames when the temporal onset of the group of stimulation pulses is equal to or nearly equal to the fixed stimulation frame onset of the one or more stimulation frames. In this example, the processor unit is configured to initiate a stimulation frame with a fixed rate at time $t_{fr}$, and where a stimulation pulse at time $t_{sp}$ arrives, the stimulation pulse is frame coded to a stimulation frame where a time difference between $t_{fr}$ and $t_{sp}$ is minimum.

For example, a group of stimulation pulses of the plurality of stimulation pulses may include a subsequent stimulation pulse and a preceding stimulation pulse, and where the subsequent stimulation pulse is subsequent in time to the preceding stimulation pulse. The second frame coding scheme may include providing aa first frame coding of the preceding stimulation pulse into a first stimulation frame of the one or more stimulation frames, and where the frame coded preceding stimulation pulses ends at an offset time, and providing, at a second frame time, a second frame coding of the subsequent stimulation pulse into a second stimulation frame of the one or more stimulation frames when the second frame time is after an analysis window which starts at the offset time and which has a maximum possible time length of a stimulation frame.

The second frame coding scheme results in a variable stimulation frame onset as the each stimulation frame is generated based on the arrival time of a stimulation pulse.

By being able to frame code with a variable stimulation frame onset, the cochlea implant system would be able to arrange the stimulation frames to code more explicitly the temporal information of an acoustical signal which comprises voice sounds without the need of a speech detection algorithm. By avoiding a speech detection algorithm, the signal processing performed by the processing unit becomes more simpler and the power consumption of the cochlea implant system is hereby reduced.

The processor unit is configured to switch between using a waveform sampling strategy, a feature extraction strategy and/or a hybrid between the waveform sampling strategy and the feature extraction strategy.

The switching mean may be configured to switch to the variable stimulation frame onset when the one or more audio components includes Temporal Fine Structure (TFS) information, and/or, the switching mean may be configured to switch to the fixed stimulation frame onset when the one or more audio components includes envelope information.

A frame time period may be defined between an onset of two subsequently stimulation frames of the one or more stimulation frames. When the frame coding has a variable stimulation frame onset, the frame time period varies between at least two subsequently stimulation frames of the one or more stimulation frames. When the frame coding has a fixed stimulation frame onset, frame time period is fixed between the one or more stimulation frames.

The following conditions may be satisfied of a stimulation frame of the plurality of stimulation frames and between each of the one or more stimulation frames;

the one or more stimulation frames may be organized in an ascending or descending order, such that a stimulation frame assigned to the most basal electrode will always be transferred first to the implantable unit.

The stimulation frame assigned to EAFx (Electrode Apical First) should always be put in front of another stimulation assigned to EAFy (another specific electrode of the electrode array) if x<y. When reaching the stimulation frame assigned to the most apical electrode, a next frame may be generated.

There are upper and lower limits for an inter-frame idle time $t_f$ ($T_{fmin} < t_f < T_{fmax}$). $t_f$ is defined as the time between the end of the last stimulation pulse in a stimulation frame and the beginning of the first stimulation pulse in the next frame.

There are upper and lower limits for an intra-frame idle time $t_p$ ($T_{pmin} < t_p < T_{pmax}$). $t_p$ is defined as the time between the end of a stimulation pulse and the beginning of a subsequent stimulation pulse in the same stimulation frame.

In a stimulation frame, if EAFy has stimulation pulse while EAFx does not (x<y), a notification pulse with duration $T_s$ should be inserted before the corresponding pulse of EAFy (the most basal electrode assigned with a stimulation pulse), to notify the implant that EAFx is skipped. If there are multiple electrodes which are unassigned with a stimulation pulse before EAFy, the same rule will be applied for each of them.

The variable stimulation frame onset may be equal to the temporal onset of the most basal electrode assigned with a stimulation pulse. For example, a first stimulation frame may begin with the stimulation pulse assigned to the most apical electrode, i.e. the electrode assigned to the lowest frequency range. The arriving time of the stimulation pulse at the most basal electrode within a stimulation frame is noted as to. Furthermore, if a stimulation pulse appears in EAFx while the previous stimulation pulse was in EAFy (x<y), and EAFx is assigned to a lower frequency range than EAFy, then the first stimulation frame is ended at the previous stimulation pulse, and a second stimulation frame is inserted to code the stimulation pulse in EAFx. This is repeated until all stimulation pulses of the plurality of stimulation pulses have been frame coded. The variable stimulation frame onset may be determined between an end of a preceding stimulation frame and the beginning of a subsequent stimulation pulse, and the beginning of the subsequent frame is determined by the offset time ($t_f$) of the stimulation pulse of the most basal electrode within the preceding stimulation frame.

An analysis window may be defined from $t_f$ and with a time length of $t_A$, where $t_A$ may be the maximum possible time length of a stimulation frame, and $t_f$ is the offset time, i.e. the time of which the stimulation pulse is off, of the stimulation pulse within the preceding stimulation frame.

Those stimulation pulses of the plurality of stimulation pulses which arrives at a time $t_{sp}$, and $t_{sp}$ is within the first analysis window, is frame coded in a sequentially and in an ascending order starting from the most apical electrode and transferred to electrode array in a descending order starting from the most basal electrode within the stimulation frame.

A low frequency group may comprise several of electrodes of the electrode array, where each is assigned to a frequency range which are within a main low frequency range. For example, electrodes EAF0 to EAF7 may be part of the low frequency group as they all are assigned to frequencies which are within the main low frequency range.

A high frequency group may comprise several of electrodes of the electrode array, where each is assigned to a frequency range which are within a main high frequency range. For example, electrodes EAF8 to EAF19 may be part of the high frequency group as they all are assigned to frequencies which are within the main high frequency range. First, all electrodes of the low frequency group which may be assigned with a stimulation pulse are coded, and when all assigned electrodes of the low frequency group are coded within the analysis window, then all electrodes of the high frequency group which may be assigned with a stimulation pulse will be coded within the analysis window. However, if an assigned electrode of the high frequency group is not able to be frame coded within the analysis window, then it is either deleted or frame coded in the next stimulation frame and within the next analysis window.

In case where stimulation pulses of the plurality pulses may be frame coded at the same, the processing unit may be configured to prioritize the frame coding of the stimulation pulses in order to avoid the conflict between the stimulation pulses. The processor unit may be configured to prioritize the stimulation pulses of the plurality of stimulation pulses to be frame coded, and the processor unit may be configured to select those stimulation pulses to be frame coded which have the highest priority. The processor unit may be configured to prioritize the stimulation pulses of the plurality of stimulation pulses based on a frequency content or energy level of each of the stimulation pulses of the plurality of stimulation pulses. By establishing the prioritization on frequency content and/or energy level the temporal information which is transferred to the auditory nerves will be of highest relevance for obtaining the best possible improvement of the users hearing capability.

A frequency content of a first stimulation pulse of the plurality of stimulation pulses includes a first range of frequencies, and a frequency content of a second stimulation pulse of the plurality of stimulation pulses includes a second range of frequencies, and the first range of frequencies includes frequencies which are lower than the frequencies of the second range of frequencies, and where the processor unit is configured to prioritize higher the first stimulation pulse before the second stimulation pulse. By, prioritizing higher the low frequency, the processing unit's ability to obtain the best pitch temporal information will not be degraded when a conflict between stimulation pulses of the plurality of stimulation pulses may appear.

The first range of frequencies and/or the second range of frequencies may include fundamental frequencies.

The processor unit may be configured to prioritize higher a first stimulation pulse of the plurality of stimulation pulses than a second stimulation pulse of the plurality of stimulation pulses when the energy level of the first stimulation pulse is higher than the second stimulation pulse. Thereby, the likelihood of prioritizing voice speech over noise in the acoustic signal will be improved with the prioritization.

The processor unit may be configured to time shift the preceding stimulation pulse of the plurality of stimulation pulses when the sample time period between the beginning of the preceding stimulation pulse and the end of the subsequent stimulation pulse of the plurality of stimulation pulses is equal to or below a sample time threshold, Thereby, no conflict between the two stimulation pulses will appear, however, the time shifting is only allowed when the amount of time shifting is below a predefined threshold.

The cochlear implant system may include a dynamic energy controller which provides a stabile supply of energy from the external unit to the implantable unit when the frame coding is based on variable stimulation frame onset.

The one or more stimulation frames may include precharge pulses which may be modified by the dynamic energy controller for obtaining a charge level within the implantable unit to be between a minimum and a maximum charge level. And/or, the dynamic energy controller is configured to insert a precharge frame between two stimulation frames if the modification of the precharge pulses is not enough to obtain the minimum charge level. The precharge frame comprises one or more precharge pulses.

In another aspect, the processor unit is configured to generate a plurality of stimulation pulses based on sampling of a full frequency range of the audio signal with a temporal onset, and one or more audio components are determined for the sampling of the full frequency range of the audio signal. The one or more audio components are more precisely determined as an acoustically interaction between the different fundamental frequency in the audio signal is taking place as no separation of the different fundamental frequency is taking place. By including the acoustical interaction the temporal information provided by the one or more audio components becomes more closer to the acoustical signal received by the receiving unit.

It is widely known that cochlear implant patients report different pitch scale if a given electrode is stimulated at different rates. If the stimulation rate of a certain electrode increases then the pitch scale will also increase in a linearly behavior up to a certain frequency, for example to around 1000 Hz. By changing the position of the electrode the same tendency is again observed, however the absolute values of pitch scales will be different. That meant that both place coding (cochlear depth) and temporal coding (stimulation rate) determine the final evaluated pitch scale by the cochlear implant patient.

The sensitivity of pitch scale to low stimulation rates is higher than high stimulation rate. For instance, the pitch scale increases from 0 to 30 if frequency increases from 100 Hz to 200 Hz. However, the pitch scale only increases 10 when the frequency of 200 Hz increases to 300 Hz.

Now, suppose that the two lowest frequency channels in a TFC coding strategy are centered at frequencies about 60 Hz and 120 Hz, respectively. Each of these channels delivers a very precise pulse events corresponding to phase and frequency of channel-based filtered audio signals (for instance, instantaneous frequency of 60.2 Hz, and 120.5 Hz). However, when the two channels are activated, the cochlear area corresponding to the first channel (i.e., centered at 60 Hz) won't really observe the precise pulse events (i.e., 62.2 Hz), but rather a summation of the two channels. The pitch perception consequence of this summation is very big as pitch scale is very sensitive to stochastic variations of low stimulation rate pulses.

As mentioned in the previous section, delivering a pitch of around 60 Hz to a cochlear implant patient may have some technical limitations: for instance high sensitivity to variations of the pitch, and interactions between channels. A same pitch scale may be obtained using different inserted electrodes in different depth of the cochlea if they are stimulated at different rates. Among all these different configurations, only one will conform physiology of a normal ear, but due to technical limitations we may go for another configuration and transfer the pitch to cochlear implant patient a bit differently as normal hearing listeners perceive pitch.

Indeed, in order to give cochlear implant patients the possibility to perform a pitch perception, it is not necessary to encode pulse events of the electrodes at fundamental and multiple frequencies of the pitch as in normal hearing listeners. Instead, the pitch perception ability may be provided to cochlear implant patients, by modifying the pulse rate of all (or some) channels of CI device in a similar manner as a function of the pitch. This is achievable by a modified CIS coding strategy that include variable stimulation rates In a CIS-based strategy, all channels are stimulated exactly with the same rate. Therefore, in such a coding strategy, interferences between adjacent channels do not modify the overall perceived pitch. In CIS-based strategy, channels have the same stimulation rate, thus the overall perceived pitch in CIS-based strategy makes a robust pitch perception that is not so sensitive to the content of the input signal. However, the problem of a classical CIS strategy is that the perceived pitch remains almost constant in different situations because the channels are stimulated always at a fixed rate.

One way to have a robust but variable pitch perception is to change the classical CIS to the modified CIS coding strategy that include variable stimulation rates. In the modified CIS coding strategy, all channels or electrodes stimulate always at a same rate, however, this rate is modulated with time as function of pitch. By this means, both place and temporal coding information is transferred to the patient.

The processor unit may include a pitch estimator configured to receive an input signal including an audio signal and estimating a pitch value of the input signal. Based on the estimated pitch value, a target stimulation rate function is determined, and this stimulation rate function may be an exponential function that may be adjusted to patient for a best performance. As stimulation rate of a first frame coding scheme (for example CIS) varies with pitch, it may have some loudness effect on the resulting pulses generated by the first frame coding scheme. The processor unit may then include a loudness compensator that is configured to compensate the loudness effect on the stimulation rate.

In one example, the stimulation rate decreases/increases with the decrease/increase of the estimated pitch. Both channels may have the same stimulation rate, and thus current spread from one electrode to another does not introduce any problem to the perceived pitch because of the pitch estimator and the loudness compensator.

The processor unit is configured to separate the channels or the electrodes of the electrode array into two main groups, a first group including channels or electrodes that are assigned to frequencies below and equal to 200 Hz, and a second group including channels or electrodes that are assigned to frequencies above 200 Hz. The two groups of electrodes may work at two different stimulation rates. For instance, stimulation rate of the second group may always be twice the first group of electrodes. In such a case, the stimulation of the first group will be closer to physiological stimulation rate. For instance, when the second group of electrodes increases the stimulation rate from 400 to 500 pps, the first group of electrodes will increase its frequency from 200 to 250 pps.

If stimulation rate of the second group is not a multiple of the first group, a physical distance on the electrode array can be created between these two groups. This reduces current interactions between the electrodes of the two groups.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

Figure 1:
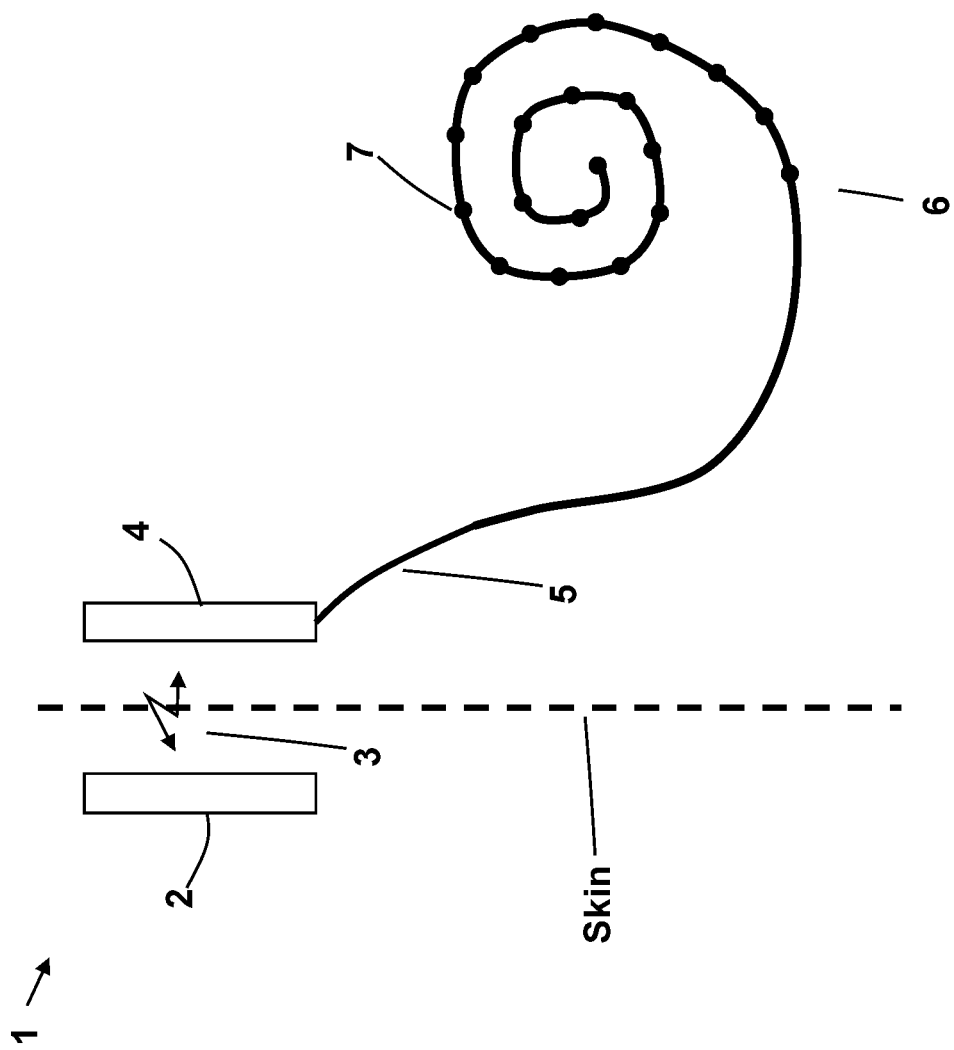
FIG. 1 illustrates a cochlear implant system.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

A hearing aid may be or include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. 'Improving or augmenting the hearing capability of a user' may include compensating for an individual user's specific hearing loss. The "hearing aid" may further refer to a device such as a hearable, an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of the middle ear of the user or electric signals transferred directly or indirectly to the cochlear nerve and/or to the auditory cortex of the user.

The hearing aid is adapted to be worn in any known way. This may include i) arranging a unit of the hearing aid behind the ear with a tube leading air-borne acoustic signals into the ear canal or with a receiver/loudspeaker arranged close to or in the ear canal and connected by conductive wires (or wirelessly) to the unit behind the ear, such as in a Behind-the-Ear type hearing aid, and/or ii) arranging the hearing aid entirely or partly in the pinna and/or in the ear canal of the user such as in an In-the-Ear type hearing aid or In-the-Canal/Completely-in-Canal type hearing aid, or iii) arranging a unit of the hearing aid attached to a fixture implanted into the skull bone such as in a Bone Anchored Hearing Aid or a Cochlear Implant, or iv) arranging a unit of the hearing aid as an entirely or partly implanted unit such as in a Bone Anchored Hearing Aid or a Cochlear implant system. The hearing aid may be implemented in one single unit (housing) or in a number of units individually connected to each other.

A "hearing system" refers to a system comprising one or two hearing aids, and a "binaural hearing system" refers to a system comprising two hearing aids where the devices are adapted to cooperatively provide audible signals to both of the user's ears. The hearing system or binaural hearing system may further include one or more auxiliary device(s) that communicates with at least one hearing aid, the auxiliary device affecting the operation of the hearing aids and/or benefitting from the functioning of the hearing aids. A wired or wireless communication link between the at least one hearing aid and the auxiliary device is established that allows for exchanging information (e.g. control and status signals, possibly audio signals) between the at least one hearing aid and the auxiliary device. Such auxiliary devices may include at least one of a remote control, a remote microphone, an audio gateway device, a wireless communication device, e.g. a mobile phone (such as a smartphone) or a tablet or another device, e.g. comprising a graphical interface, a public-address system, a car audio system or a music player, or a combination thereof. The audio gateway may be adapted to receive a multitude of audio signals such as from an entertainment device like a TV or a music player, a telephone apparatus like a mobile telephone or a computer, e.g. a PC. The auxiliary device may further be adapted to (e.g. allow a user to) select and/or combine an appropriate one of the received audio signals (or combination of signals) for transmission to the at least one hearing aid. The remote control is adapted to control functionality and/or operation of the at least one hearing aid. The function of the remote control may be implemented in a smartphone or other (e.g. portable) electronic device, the smartphone/electronic device possibly running an application (APP) that controls functionality of the at least one hearing aid.

In general, a hearing aid includes i) a receiving unit such as a microphone for receiving an acoustic signal from a user's surroundings and providing a corresponding input audio signal, and/or ii) a receiving unit for electronically receiving an input audio signal. The hearing aid further includes a signal processing unit for processing the input audio signal and an output unit for providing an audible signal to the user in dependence on the processed audio signal.

The receiving unit may include multiple input microphones, e.g. for providing direction-dependent audio signal processing. Such directional microphone system is adapted to (relatively) enhance a target acoustic source among a multitude of acoustic sources in the user's environment and/or to attenuate other sources (e.g. noise). In one aspect, the directional system is adapted to detect (such as adaptively detect) from which direction a particular part of the microphone signal originates. This may be achieved by using conventionally known methods. The signal processing unit may include an amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air borne acoustic signal transcutaneously or percutaneously to the skull bone or a vibrator for providing a structure-borne or liquid-borne acoustic signal. In some hearing aids, the output unit may include one or more output electrodes for providing the electric signals such as in a Cochlear Implant.

A Cochlear Implant typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing aid comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

Now referring to FIG. 1, which illustrates a cochlear implant system 1 which includes an external unit 2 and an implantable unit 4 which are able to communicate transcutaneoulsy 3 through the skin of the user of the system 1. The implantable unit 4 is connected to an electrode array 5 which is configured to be inserted into the cochlea 6 of the user. The electrode array may include a plurality of electrodes 7.

Figure 2A:
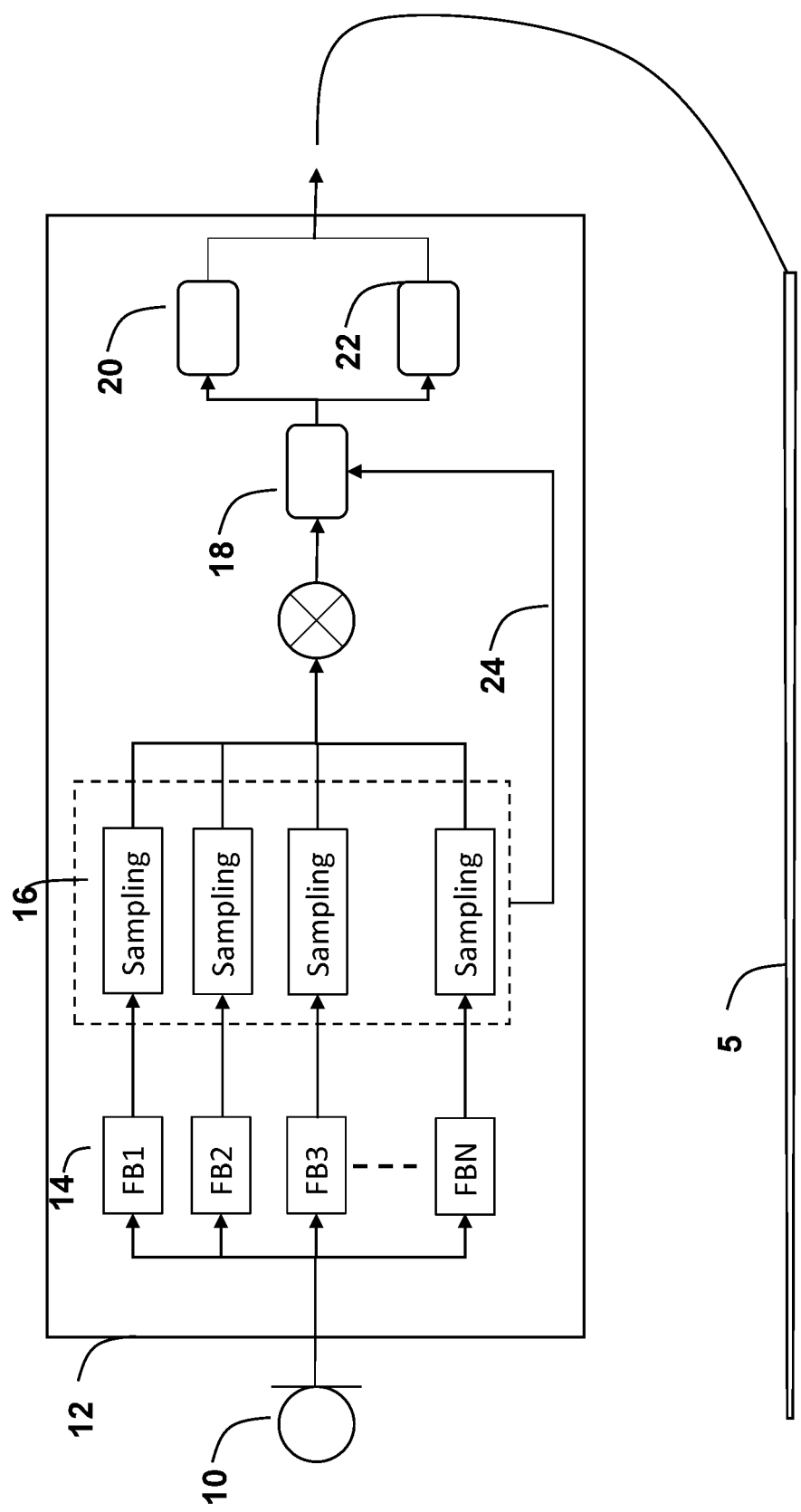
FIGS. 2A and 2B illustrates a cochlear implant system.
Figure 2B:
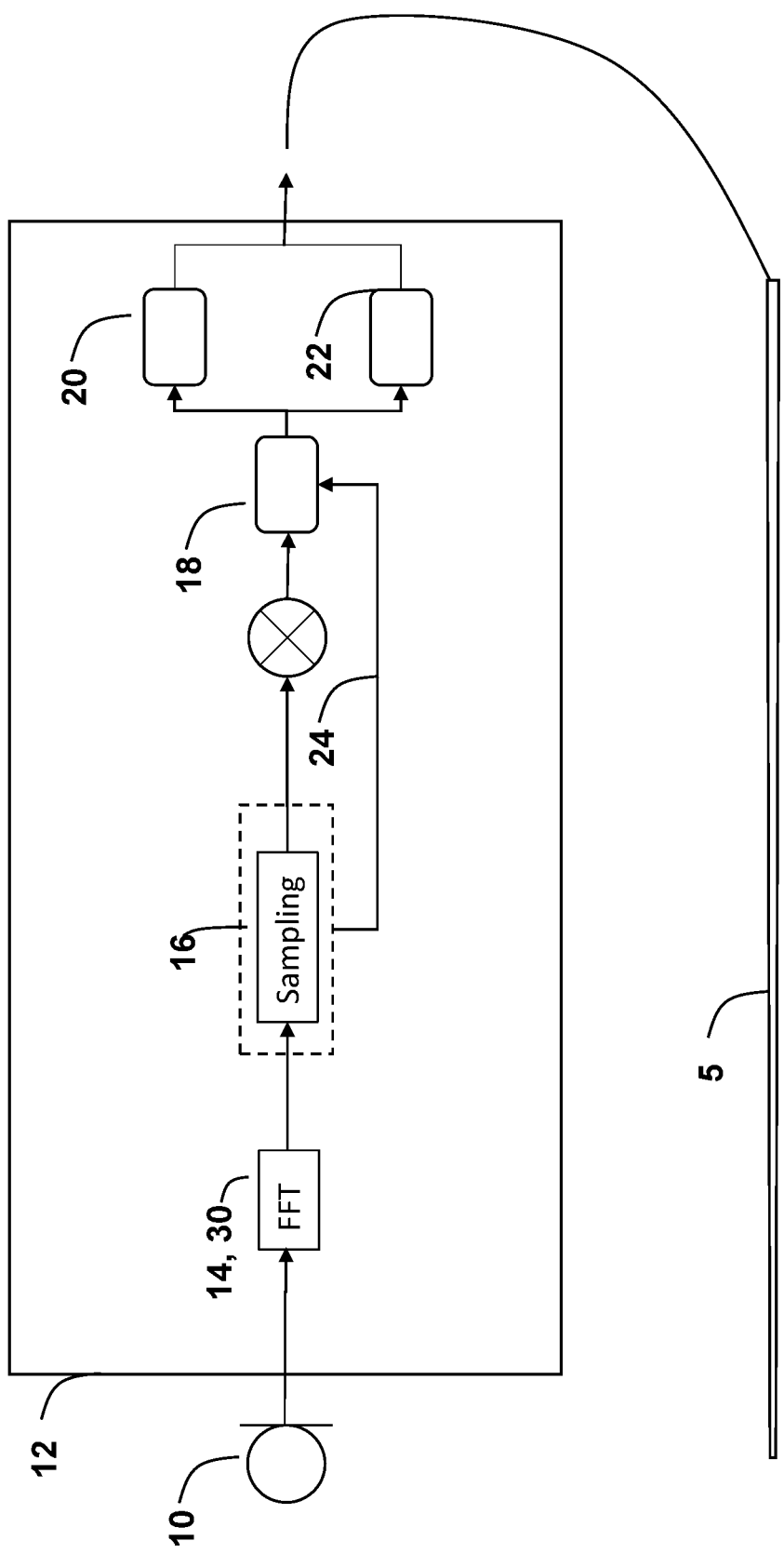

FIGS. 2A and 2B illustrate different examples of the cochlear implant system 1 which comprises a receiving unit 10 configured to receive an acoustical signal and transmit an audio signal based on the acoustical signal, and wherein this specific example, the receiving unit includes a microphone. In FIG. 2A, the system 1 includes further a processor unit 12 which is configured to receive and divide the audio signal into a plurality of band limited audio signals (FB1, FB2, FB3, and FBN) via a filter bank 14 and to generate a plurality of stimulation pulses based on sampling 16 of the plurality of band limited audio signals (FB1, FB2, FB3, and FBN). Each of the plurality of band limited audio signals (FB1, FB2, FB3, and FBN) is sampled with a temporal onset. and one or more audio components 24 are determined for each of the plurality of band limited audio signals via the sampling, The processor unit 12 is connected to an electrode array 5 including a plurality of electrodes 7, and wherein the processor unit 12 includes a switching mean 18 configured to switch between using a fixed stimulation frame onset 20 or a variable stimulation frame onset 22 for frame coding the plurality of stimulation pulses into one or more stimulation frames, wherein the switching mean 18 is configured to switch between the fixed stimulation frame onset 20 and the variable stimulation frame onset 22 based on the one or more audio components 24, and wherein the electrode array 5 is configured to stimulate auditory nerves of a user of the cochlear implant system 1 based on the frame coded plurality of stimulation pulses. The one or more audio components are determined by the sampling process 16, where the one or more audio components may include at least one of a fundamental frequency, harmonic frequencies relative to the fundamental frequency of the audio signal, energy at and around the fundamental frequency and harmonics of the audio signal, and/or phase at and around the fundamental frequency and harmonics of the audio signal.

Alternatively, the switching mean 18 is configured to switch to the variable stimulation frame onset when the one or more audio components includes Temporal Fine Structure (TFS) information of the acoustical signal, and/or, the switching mean is configured to switch to the fixed stimulation frame onset when the one or more audio components includes envelope information of the acoustical signal.

In FIG. 2B the filter bank includes a filter bank 14 which includes a Fast Fourier transformation unit 30 which is configured to perform a fourier transformation of a full frequency range of the audio signal, which then results in a sampling of the full frequency range audio signal, and where the one or more audio components are determined based on the sampling of the full frequency range of the audio signal.

Figure 3A:
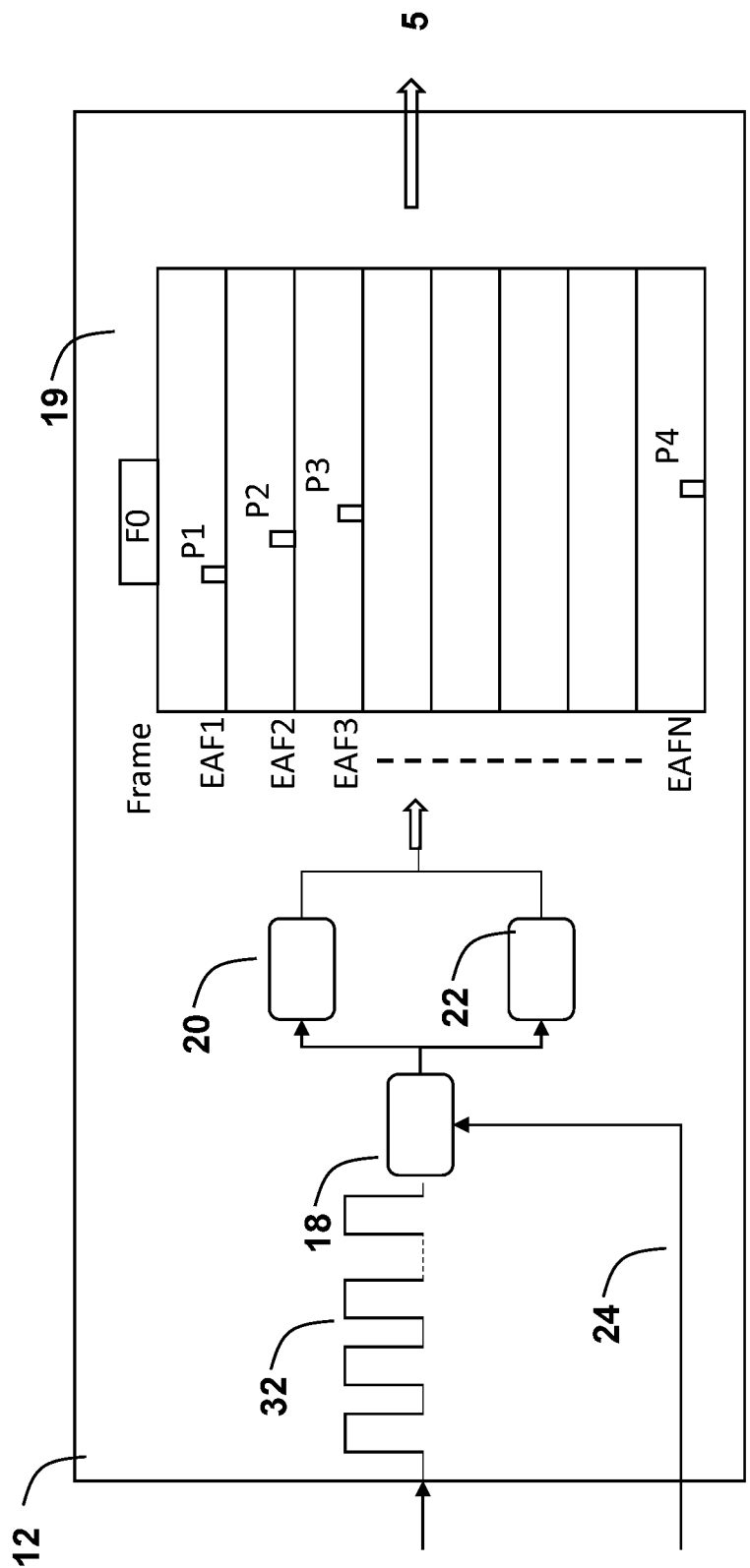
FIGS. 3A to 3D illustrates different examples of frame coding.

FIGS. 3A to 3D illustrate different examples of frame coding performed by the processor unit 12. In FIG. 3A, the switching unit 18 receives the plurality of stimulation pulses 32 from the plurality of band limited audio signals (FB1 to FBN) and frame codes the plurality of stimulation pulses 32 into a stimulation frame F0. In this specific example, the most apical electrode, EAF1, and EAF2, EAF3 and EAFN are activated by receiving a stimulation pulse (P1-P4) of the plurality of stimulation pulses 32. EAF1 is stimulating first and EAFN is stimulating at the end of the stimulation frame F0. The stimulation pulses (P1-P4) are transmitted to the electrode array 5 such that the most basal electrode EAFN will always be transferred first to the implantable unit and with the same timing between the stimulating pulses as illustrated in the electrodogram 19.

Figure 3B:
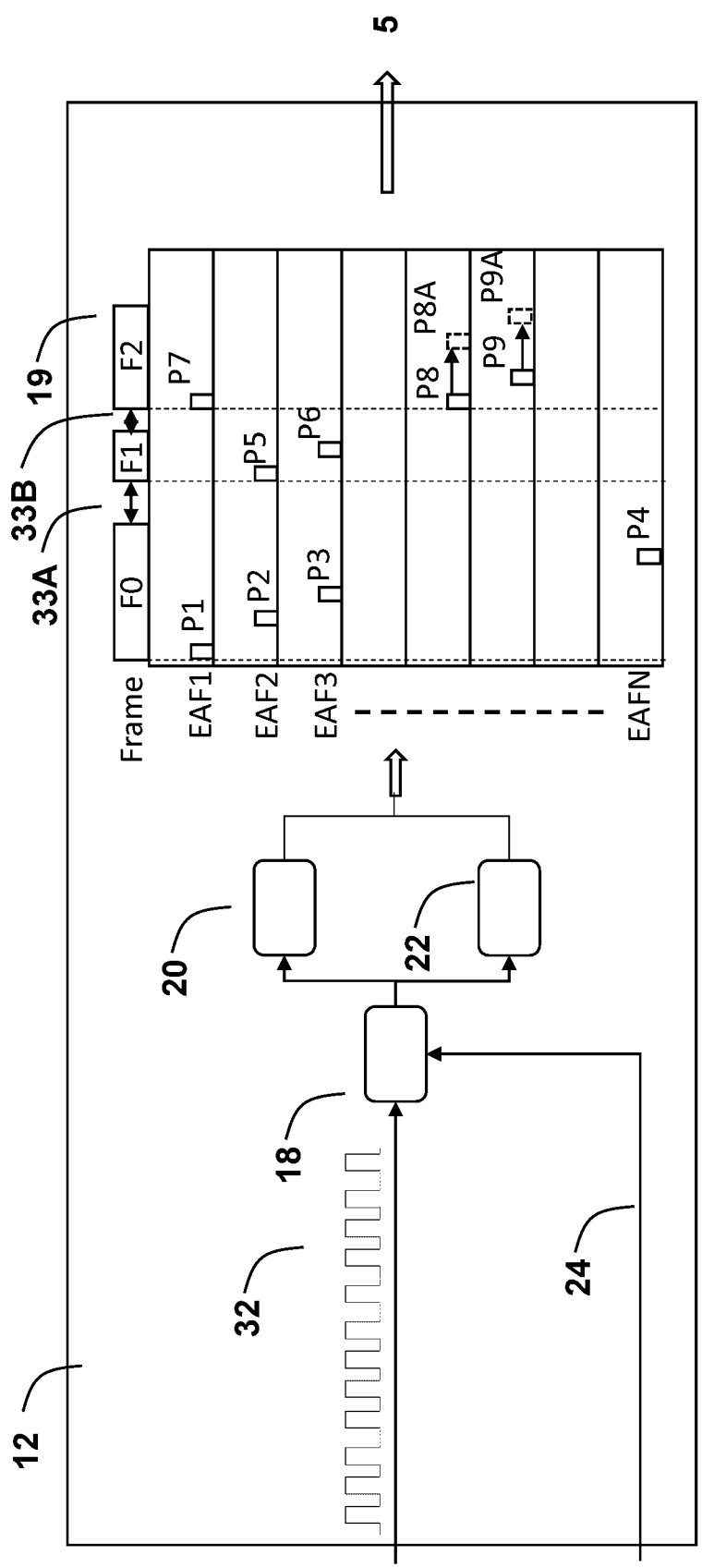

FIG. 3B illustrates an example where the switching means 18 is using variabfale stimulation frame onset 22 for frame coding the plurality of stimulation pulses 32. The processor unit 12 frame codes a first group of stimulation pulses (P1 to P4) into a first stimulation frame F0, and a second stimulation frame F1 is generated as the next stimulation pulse P5 to be frame coded is more apical in frequency than the previous frame coded stimulation pulse P4. The processor unit 12 frame codes within the second stimulation frame F1 a second group of stimulation pulses including P5 and P6, and a third stimulation frame F2 is generated as the next stimulation pulse P7 is more apical in frequency than the previous frame coded stimulation pulse P6. The processor unit frame codes within the third stimulation frame F2 a third group of stimulation pulses including P7 to P9, however, a collision is seen between all three stimulation pulses of the third stimulation frame F2. The processor unit is configured to time shift the subsequent stimulation P8 to P8A such that a pulse time difference between the beginning of a preceding stimulation pulse P8 and the end of the subsequent stimulation pulse P7 is above a maximum time difference or is below a minimum time difference. In this specific example P8 is time shifted to P8A and P9 is time shifted to P9A. The result of the frame coding of the plurality of stimulation pulses 32 is a varying frame time period (33A and 33B) between the one or more stimulation frames (F0, F1, F2).

Figure 3C:
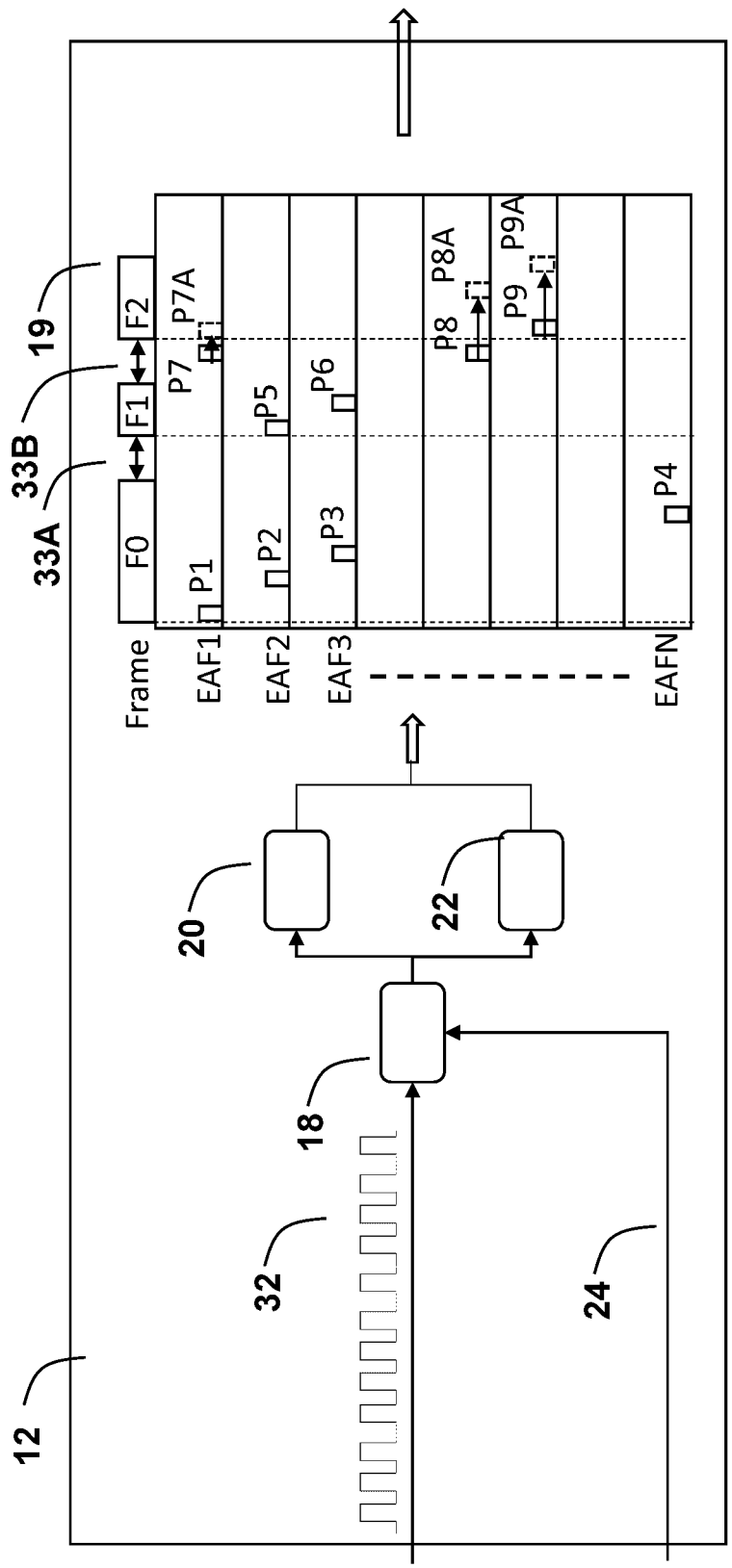

FIG. 3C illustrates an example where the switching means 18 is using fixed stimulation frame onset 20 for frame coding the plurality of stimulation pulses 32. The processor unit 12 frame codes a first group of stimulation pulses (P1 to P4) into a first stimulation frame F0, and a second stimulation frame F1 is generated as the next stimulation pulse P5 to be frame coded is more apical in frequency than the previous frame coded stimulation pulse P4. The processor unit 12 frame codes within the second stimulation frame F1 a second group of stimulation pulses including P5 and P6, and a third stimulation frame F2 is generated as the next stimulation pulse P7 is more apical in frequency than the previous frame coded stimulation pulse P6. Since the one or more audio components have dictated the switching mean to switch to fixed stimulation frame onset 20, the processor unit needs to time shift the stimulation pulse P7 such that the frame time period (33A, 33B) between the stimulation frames (F0, F1, F2) keeps fixed (33B), and furthermore, the processor unit has to time shifts P8 and P9 in order to keep a correct timing between the other stimulation pulses P8 and P9 such that the most basal electrode will always be transferred first to the implantable unit.

Figure 3D:
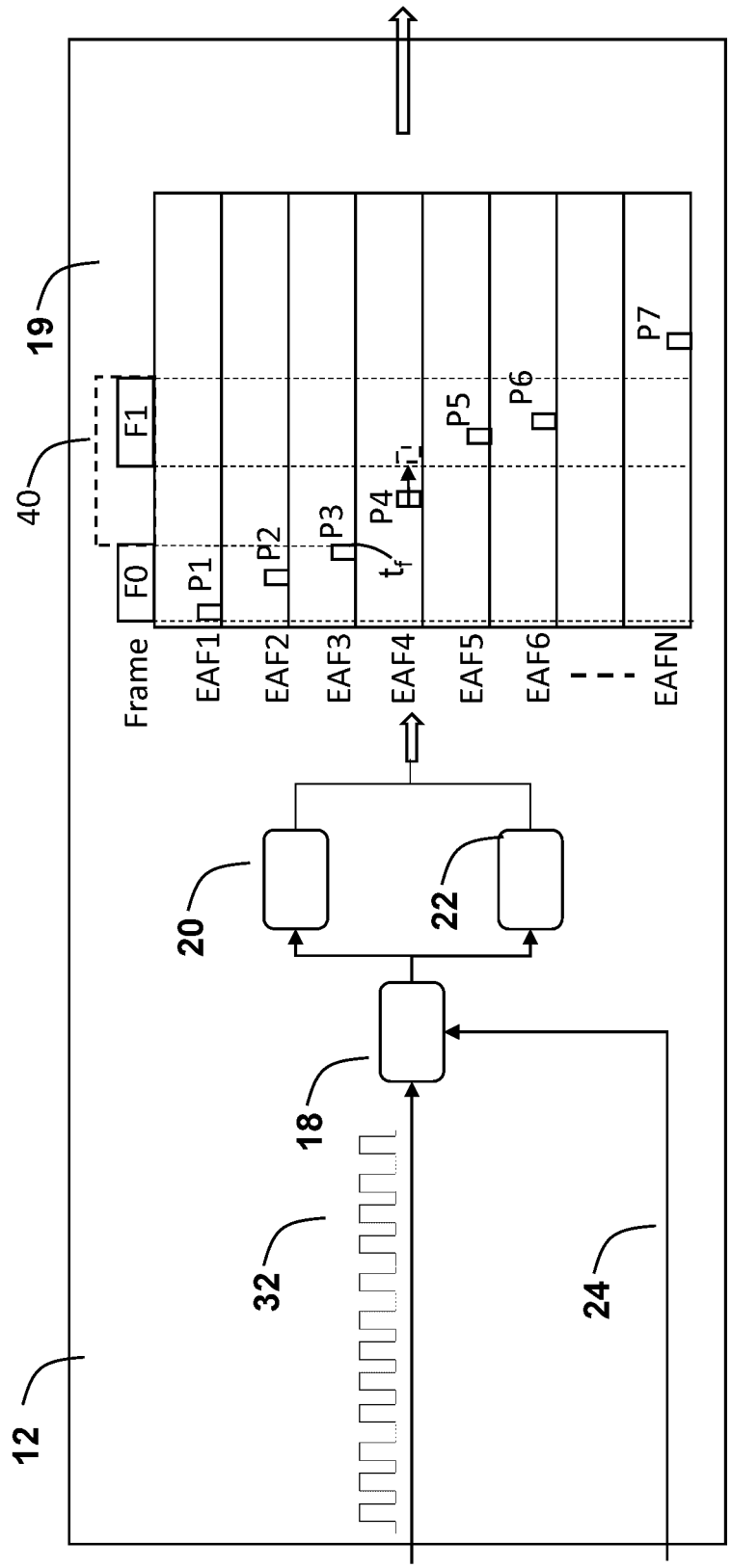

In both the variable and fixed stimulation frame onset examples an analysis window 49 determines which of the stimulation pulses 32 are going to be frame coded within a next stimulation frame F1. In FIG. 3D, the analysis window starts at the offset time h of the most basal stimulation pulse P3 of the previous stimulation frame F0, and has a maximum possible time length of a stimulation frame. In this example, the stimulation pulses P1 to P3 are frame coded within the first stimulation frame F0, and the stimulation pulses which are within the analysis window 40 are frame coded within the second stimulation frame F1, and the stimulation pulse P7 which is outside the analysis window 40 will be frame coded in a next stimulation frame (not shown).

Figure 4B:
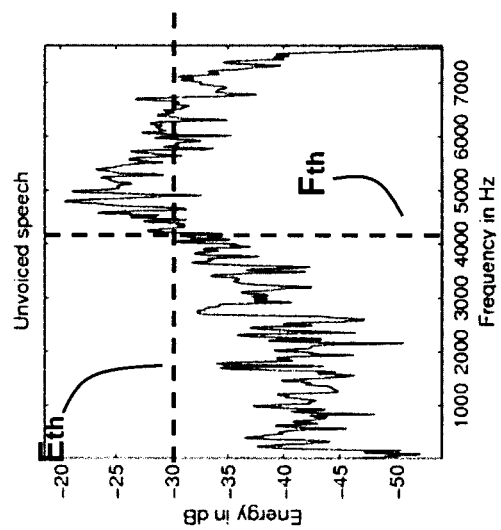
FIGS. 4A and 4B illustrates an example of an acoustic spectrum of a voice speech and unvoiced speech.
Figure 4A:
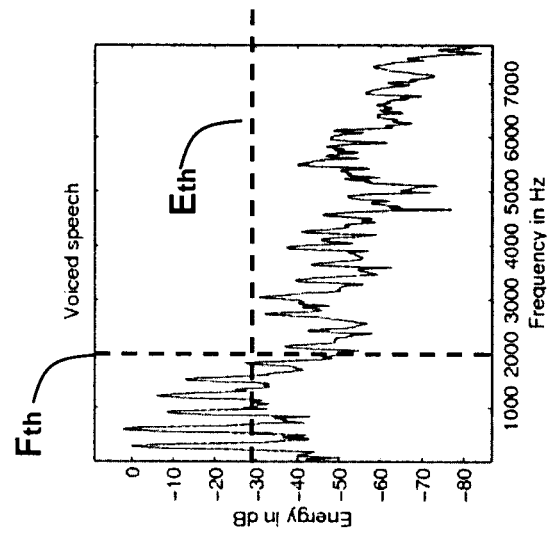

FIGS. 4A and 4B illustrate an example of an acoustic spectrum of a voice speech and an unvoiced speech which includes a frequency threshold $F_{th}$ and an energy threshold Eth for deciding whether the audio signal, and the one or more audio components 24 relates to voice or unvoiced speech. In both examples the energy threshold Eth is set to −30 dB of normalized speech energy signal and the frequency threshold $F_{th}$ is set to 2000 Hz, and in FIG. 4A, it is seen that for a voiced speech the energy peaks above Eth appears at frequencies below the frequency threshold, and in FIG. 4B, it is seen that for an unvoiced speech the energy peaks above Eth appears at frequencies above the frequency threshold. During the sampling of each of the plurality band limited audio signals one or more audio components are determined for each of the plurality of stimulation pulses, and in this example, at least one stimulation pulse of the plurality of stimulation pulses has multiple audio components including a fundamental frequency and an energy at the fundamental frequency. The multiple audio components relate to voiced speech as the energy at the fundamental frequency is above Eth, and the fundamental frequency is below $F_{th}$, and thereby, the switching unit makes sure that the frame coding provided by the processor unit is using variable stimulation frame onset.

In another example, if at least one of the plurality of stimulation pulses has an energy at the fundamental frequency which is above Eth, and the fundamental frequency is below $F_{th}$, the plurality of stimulation pulses are all frame coded using variable stimulation rate.

In yet another example, if at least one stimulation pulse of a group of stimulation pulses of the plurality of stimulation pulses has an energy at the fundamental frequency which is above Eth, and the fundamental frequency is below $F_{th}$, the group of stimulation pulses are all frame coded using variable stimulation rate.

Figure 5:
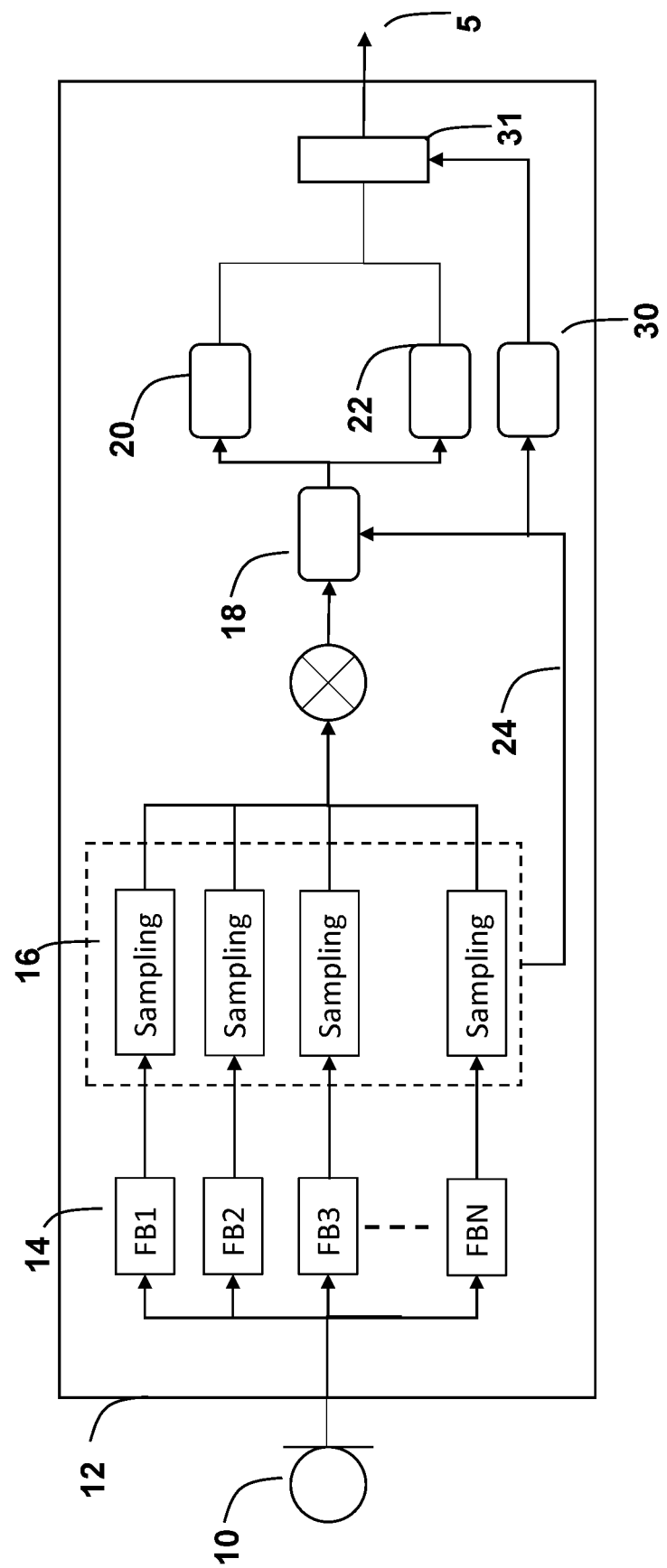
FIG. 5 illustrates an example of a cochlear implant system.

FIG. 5 illustrates an example of the cochlear implant system. As the stimulation rate varies along with the content of the one or more audio components 24, e.g., the pitch, will have some loudness effect on the resulting stimulation pulse. In this example the processor unit includes a loudness compensator 30 configured to compensate for the loudness effect based on a measure of the one or more audio components 24. For example, the processor unit 12 is configured to measure the one or more audio components, and based on the measure the processing unit 12 is configured to determine a compensation 30 of the loudness effect (i.e. variation in loudness due to variation in stimulation rate) and to determine a stimulation rate for the variable stimulation frame onset 22. In FIG. 5, the loudness compensator receives the one or more audio components 24 and provides the compensation of the loudness effect to the frame coding 31 of the plurality of stimulation pulses. In this example, the variable stimulation frame onset 22 determines the stimulation rate based on the one or more audio components 24.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element, but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects. Reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A cochlear implant system comprising:
   a receiver configured to receive an acoustical signal and transmit an audio signal based on the acoustical signal,
   a processor configured to receive and divide the audio signal into a plurality of band limited audio signals and to generate a plurality of stimulation pulses based on sampling of the plurality of band limited audio signals, and wherein each of the plurality of band limited audio signals is sampled with a temporal onset, and one or more audio components are determined for each of the sampled plurality of stimulation pulses, and
   an electrode array including a plurality of electrodes,
   wherein the processor is configured to switch between using a fixed stimulation frame onset or a variable stimulation frame onset for frame coding the plurality of stimulation pulses into one or more stimulation frames, wherein the processor is configured to switch between the fixed stimulation frame onset and the variable stimulation frame onset based on the one or more audio components, and wherein the electrode array is configured to stimulate auditory nerves of a user of the cochlear implant system based on the frame coded plurality of stimulation pulses, and
   wherein the processor is configured to generate a sequence of events for each of the plurality of band limited audio signals, and where each event of the sequence of events is determined when a phase of the band limited audio signal exceeds a phase threshold, and wherein the phase threshold is any value between 0 and $2\pi$, and the temporal onset is equal to an event rate of the sequence of event.

2. A cochlear implant system according to claim 1, when using the fixed stimulation frame onset, the stimulation frame onset is the same between each of the one or more stimulation frames, and when using the variable stimulation frame onset, the stimulation frame onset is varying between each of the one or more stimulation frames.

3. A cochlear implant system according to claim 1, wherein the one or more audio components are determined by the processor, and wherein the one or more audio components include at least one of a fundamental frequency, harmonic frequencies relative to the fundamental frequency of the audio signal, energy at the fundamental frequency and harmonics of the audio signal, and/or phase at the fundamental frequency and harmonics of the audio signal.

4. A cochlea implant system according to claim 3, wherein the processor is configured to switch to the fixed stimulation frame onset when the fundamental frequency is above a frequency threshold, and the processor is configured to switch to the variable stimulation frame onset when the fundamental frequency is below the frequency threshold, or the processor is configured to switch to the fixed stimulation frame onset when the energy in dB is above an energy threshold, and the processor is configured to switch to the variable stimulation frame onset when the energy in dB is below the energy threshold.

5. A cochlea implant system according to claim 3, wherein the processor is configured to switch to the fixed stimulation frame onset when the audio components relate to an unvoiced speech, or switch to the variable stimulation frame onset when the audio components relate to a voiced speech.

6. A cochlea implant system according to claim 1, wherein the processor is configured to provide a first frame coding scheme and a second frame coding scheme for frame coding the plurality of stimulation pulses into the one or more stimulation frames for the fixed stimulation frame onset and the variable stimulation frame onset, respectively, and where the first frame coding scheme is different from the second frame coding scheme.

7. A cochlea implant system according to claim 6, wherein the first frame coding scheme provides frame coding of a group of stimulation pulses of the plurality of stimulation pulses to a stimulation frame when the temporal onset of the group of stimulation pulses is equal to or nearly equal to the fixed stimulation frame onset of the one or more stimulation frames.

8. A cochlea implant system according to claim 6, wherein a group of stimulation pulses of the plurality of stimulation pulses includes a subsequent stimulation pulse and a preceding stimulation pulse, and where the subsequent stimulation pulse is subsequent in time to the preceding stimulation pulse to be transferred to the electrode array, where the second frame coding scheme including:
providing a first frame coding of the preceding stimulation pulse into a first stimulation frame of the one or more stimulation frames, and where the frame coded preceding stimulation pulse ends at an offset time $t_f$,
providing, at a second frame time, a second frame coding of the subsequent stimulation pulse into a second stimulation frame of the one or more stimulation frames when the second frame time is after an analysis window which starts at the offset time and which has a maximum possible time length of a stimulation frame.

9. A cochlea implant system according to claim 1, wherein the processor is configured to switch to the variable stimulation frame onset when the one or more audio components includes Temporal Fine Structure (TFS) information of the acoustical signal, and/or, the processor is configured to switch to the fixed stimulation frame onset when the one or more audio components includes envelope information of the acoustical signal.

10. A cochlea implant system according to claim 1, wherein the processor is configured to prioritize the stimulation pulses of the plurality of stimulation pulses to be frame coded, and where the processor is configured to select those stimulation pulses to be frame coded which have the highest priority.

11. A cochlea implant system according to claim 10, wherein the processor is configured to prioritize the stimulation pulses of the plurality of stimulation pulses based on a frequency content or energy level of each of the stimulation pulses of the plurality of stimulation pulses.

12. A cochlea implant system according to claim 11 where a first frequency content of a first stimulation pulse of the plurality of stimulation pulses includes a first range of frequencies, and a second frequency content of a second stimulation pulse of the plurality of stimulation pulses includes a second range of frequencies, and the first range of frequencies includes frequencies which are lower than the frequencies of the second range of frequencies, and where the processor is configured to prioritize higher the first stimulation pulse before the second stimulation pulse.

13. A cochlea implant system according to claim 11, where the processor is configured to prioritize higher a first stimulation pulse of the plurality of stimulation pulses than a second stimulation pulse of the plurality of stimulation pulses when the energy level of the first stimulation pulse is higher than the second stimulation pulse.

14. A cochlea implant system according to claim 8, within a stimulation frame of the one or more stimulation frames, the processor is configured to time shift the preceding stimulation pulse when a pulse time difference between a beginning of the preceding stimulation pulse and the end of the subsequent stimulation pulse is above a maximum time difference or is below a minimum time difference.

15. A cochlear implant system according to claim 2, wherein the one or more audio components are determined by the processor, and wherein the one or more audio components include at least one of a fundamental frequency, harmonic frequencies relative to the fundamental frequency of the audio signal, energy at the fundamental frequency and harmonics of the audio signal, and/or phase at the fundamental frequency and harmonics of the audio signal.

16. A cochlea implant system according to claim 2, wherein the processor is configured to provide a first frame coding scheme and a second frame coding scheme for frame coding the plurality of stimulation pulses into the one or more stimulation frames for the fixed stimulation frame onset and the variable stimulation frame onset, respectively, and where the first frame coding scheme is different from the second frame coding scheme.

17. A cochlear implant system comprising:
receiver configured to receive an acoustical signal and transmit an audio signal based on the acoustical signal,
a processor configured to receive and divide the audio signal into a plurality of band limited audio signals and to generate a plurality of stimulation pulses based on sampling of the plurality of band limited audio signals, and wherein each of the plurality of band limited audio signals is sampled with a temporal onset, and one or more audio components are determined for each of the sampled plurality of stimulation pulses, and
an electrode array including a plurality of electrodes,
wherein the processor is configured to switch between using a fixed stimulation frame onset or a variable stimulation frame onset for frame coding the plurality of stimulation pulses into one or more stimulation frames, wherein the processor is configured to switch between the fixed stimulation frame onset and the variable stimulation frame onset based on the one or more audio components, and wherein the electrode array is configured to stimulate auditory nerves of a user of the cochlear implant system based on the frame coded plurality of stimulation pulses, and wherein the processor is configured to provide a first frame coding scheme and a second frame coding scheme for frame coding the plurality of stimulation pulses into the one or more stimulation frames for the fixed stimulation frame onset and the variable stimulation frame onset, respectively, and where the first frame coding scheme is different from the second frame coding scheme.

* * * * *